(12) United States Patent  
Glassman et al.

(10) Patent No.: US 9,540,462 B2  
(45) Date of Patent: Jan. 10, 2017

(54) CATECHOL-RICH POLYMERS FROM N-SUBSTITUTED MALEIMIDES

(71) Applicant: Massachusetts Institute of Technology, Cambridge, MA (US)

(72) Inventors: Matthew J. Glassman, Yorba Linda, CA (US); Bradley D. Olsen, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/960,799

(22) Filed: Dec. 7, 2015

(65) Prior Publication Data

US 2016/0194415 A1    Jul. 7, 2016

Related U.S. Application Data

(60) Provisional application No. 62/088,111, filed on Dec. 5, 2014.

(51) Int. Cl.
  *C08G 73/00* (2006.01)
  *C08F 22/40* (2006.01)
  *C07D 207/452* (2006.01)

(52) U.S. Cl.
  CPC ........... *C08F 22/40* (2013.01); *C07D 207/452* (2013.01)

(58) Field of Classification Search
  CPC ............................ C08F 22/40; C07D 207/452
  See application file for complete search history.

(56) References Cited

U.S. PATENT DOCUMENTS

2005/0014803 A1    1/2005  Martinez et al.
2008/0275057 A1   11/2008  Kawabe et al.

FOREIGN PATENT DOCUMENTS

| CN | 103468031 | * 11/2014 | ............... C09C 3/08 |
| EP | 0333522 A2 | 9/1989 | |
| WO | WO-2013/020024 A2 | 2/2013 | |

OTHER PUBLICATIONS

International Search Report issued by the International Searching Authority, dated Apr. 8, 2016, in corresponding International Application No. PCT/US2015/064214.

* cited by examiner

*Primary Examiner* — Shane Fang
(74) *Attorney, Agent, or Firm* — Dana M. Gordon; Foley Hoag LLP

(57) ABSTRACT

Monomers and polymers, and a method of making polymers that retain the ability of the polymer to form reversible and irreversible bonds are provided. Gels comprising the polymers have the ability to coordinate metal ions and bind biopolymers.

20 Claims, 8 Drawing Sheets

A)

B)

C)

A)

B)

A)

B)

C)

D)

A)

B)

C)

CATECHOL-RICH POLYMERS FROM N-SUBSTITUTED MALEIMIDES

RELATED APPLICATION

This application claims the benefit of priority to U.S. Provisional Patent Application Ser. No. 62/088,111, filed Dec. 5, 2014.

GOVERNMENT SUPPORT

This invention was made with government support under W911NF-07-D-0004, awarded by the Army Research Office. The government has certain rights in the invention.

BACKGROUND OF THE INVENTION

Catechol functional groups are of broad interest to the polymer community due to their unique physical and chemical bonding behavior, having the potential to serve as adhesive or toughening moieties in various soft material systems. Catechols have been introduced into macromolecules in various strategies. See for example, Farure et al., *Progess in Polymer Science*, 38(1):236-270 (2012). A common approach is to couple the amino acid L-3,4-dihydroxyphenylalanine (DOPA) to polymers via carboxylic acid or amine-containing sidechains. See Holten-Andersen, et al. *PNAS*, 108(7):2651-2655 (2011). Alternatively, a number of vinyl-based monomers with protected or unprotected catechol substituents have been polymerized directly under free radical conditions.

However, one major difficulty of polymerizing catechol-functionalized monomers is control over their solubility in water at physiological pH when targeting high fractions of catechol. Homopolymers of some vinyl-based catechol-containing monomers are typically reported to be insoluble in water below a pH of approximately 10. See Guvendiren et al., *Biomacromolecules* 9(1):122-128 (2008). Solubility is also an issue for post-functionalized polymers, as a large conversion of acid or amine sidechains can lead to chain collapse under aqueous conditions at mild pH. Nevertheless, a number of applications for lightly-to-moderately-functionalized catechol polymers are actively being explored, including the development of PEG-based tissue adhesives for wound sealing during surgical operations. See Bilic et al., *American Journal of Obstetrics and Gynecology*, 202 (1):85.e1-85.e9 (2010).

When oxidized, catechols can couple to themselves, or react with various nucleophiles present in extracellular matrix proteins on the tissue surface. Thus, catechol-functionalized polymers may be used in many diverse applications, including biological and chemical sensing (See Ruan et al., *Sensors and Actuators B: Chemical*. 2013, 177: 826-832), incorporation into polyelectrolyte multilayers (See Min et al., *Chem. Mater.* 2011, 23 (24): 5349-5357), as components of antifouling strategies, and as adhesives for marine and biomedical applications (See Lee et al., *Annu. Rev. Mater. Res.* 2011 41: 99-132). Retaining the ability to process the highly-functionalized polymers under aqueous, physiological conditions will be transformative for many of these application areas. Water-processable, catechol-functionalized polymers in use today typically are synthesized via post-functionalization of a water-soluble polymer. Because the catechol moiety itself is insoluble except under strongly basic conditions (pH>10), this generally leads to an upper limit on the catechol content of these polymers.

Therefore, there is a need for a highly soluble, catechol-rich polymer that can be synthesized without interfering with the catechols' ability to form reversible and irreversible intermolecular bonds.

SUMMARY OF THE INVENTION

In one aspect, the present invention provides a compound represented by Formula I:

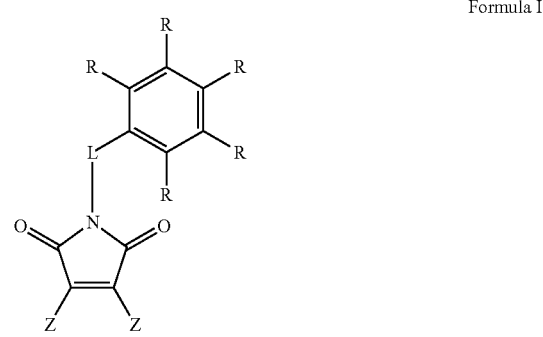

Formula I wherein, independently for each occurrence:

Z is hydrogen or optionally substituted alkyl, acyl, acyloxy, aryl, sulfonate, sulfone, sulfoxide, or sulfonamide;

L is $-(C(R^1)_2)_n-$, or $-(C(R^1)_2)_nO-$;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and $-OR^2$; provided that two instances of R represent $-OR^2$;

$R^1$ is hydrogen or alkyl;

$R^2$ is hydrogen or optionally substituted alkyl, acyl, or aryl; and n is 1, 2, 3, 4, 5, or 6.

In another aspect, the invention provides a method of preparing a polymer comprising a plurality of polymer blocks represented by Formula II:

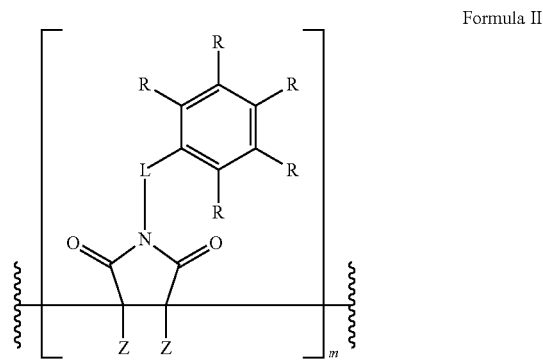

Formula II comprising the step of combining a compound of any one of claims 1-13, and a free radical initiator;

wherein, independently for each occurrence:

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl;

n is 1, 2, 3, 4, 5, or 6; and m is 1 to 500,000.

In another aspect, the invention provides a polymer, comprising a plurality of polymer blocks represented by Formula II:

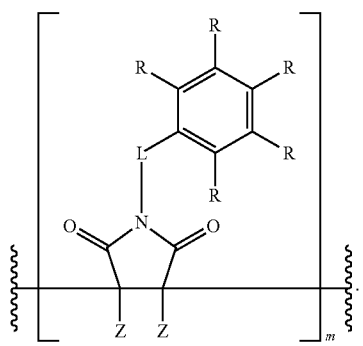

Formula II

In another aspect, the invention provides a polymer, comprising a plurality of polymer blocks represented by Formula III:

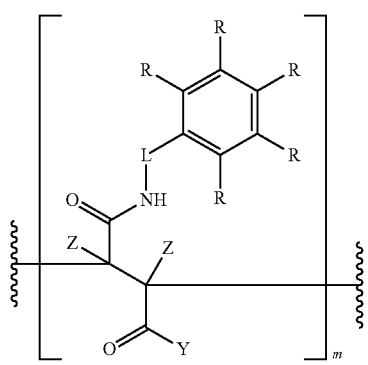

Formula III wherein, independently for each occurrence:

Y is —$OR^3$ or —$N(R^1)(R^2)$;

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl;

$R^3$ is hydrogen or alkyl;

n is 1, 2, 3, 4, 5, or 6; and m is 1 to 500,000.

In another aspect, the invention provides a polymer, comprising a first polymer block; and a second polymer block; wherein said first polymer block is a polymer of any one of the polymers comprising Formula II; and said second polymer block is a polymer of any one of the polymers comprising Formula III.

In another aspect, the invention provides a gel, comprising a polymer of any one of the above-mentioned polymers comprising Formula III; and a second polymer.

In another aspect, the invention provides a complex coacervate, comprising a polymer of any one of the above-mentioned polymers; and a cationic polymer.

DETAILED DESCRIPTION OF THE INVENTION

Overview

Figure 1:
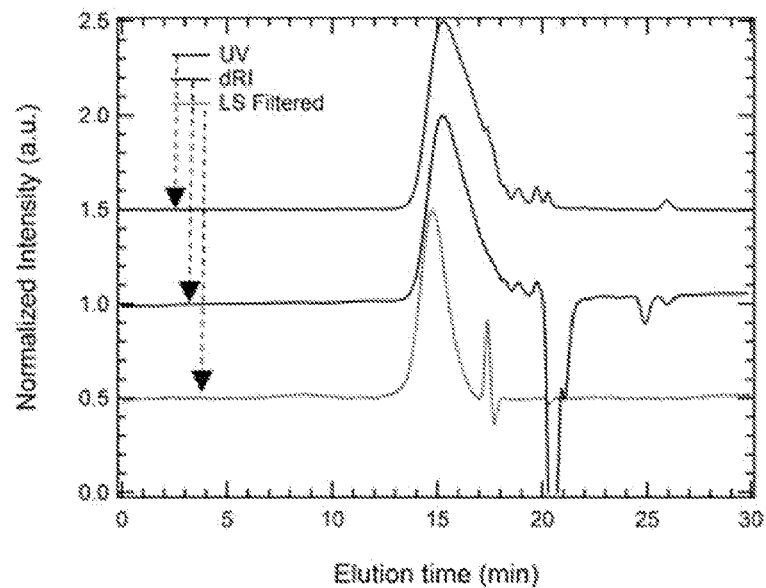
FIG. 1 depicts characterization data for certain polymers of the invention. Panel A depicts the gel permeation chromatograph of poly(N-maleimido-O,O'-diacetyldopamine) after ether precipitation. The NMR spectra of poly(N-maleimido-O,O'-diacetyldopamine) are depicted: after ether precipitation (panel B), and after hydrolysis via TFA/HBr incubation at room temperature (panel C).
Figure 1:
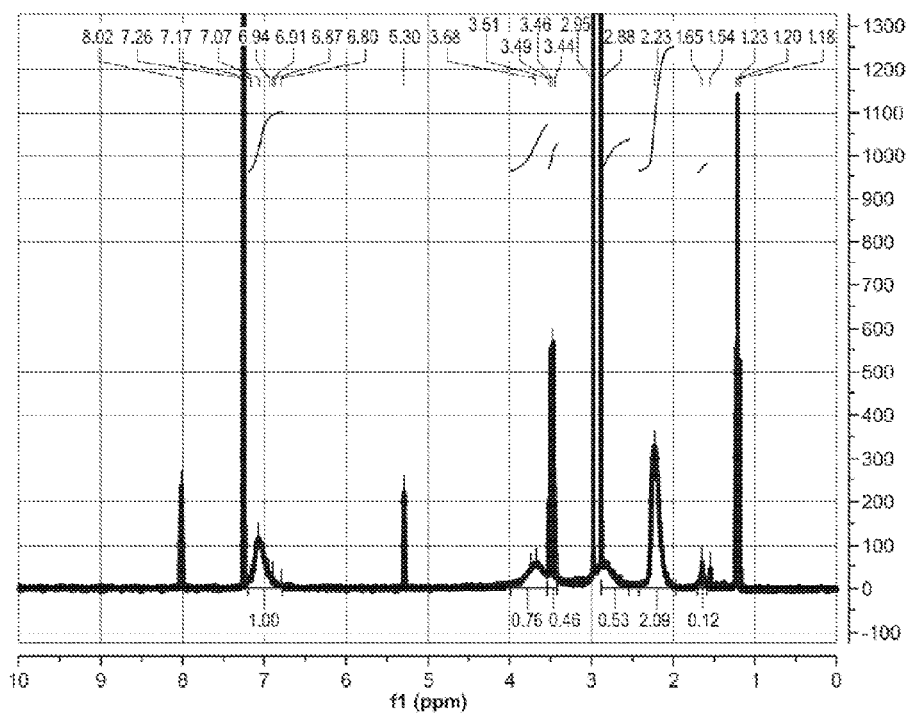
Figure 1:
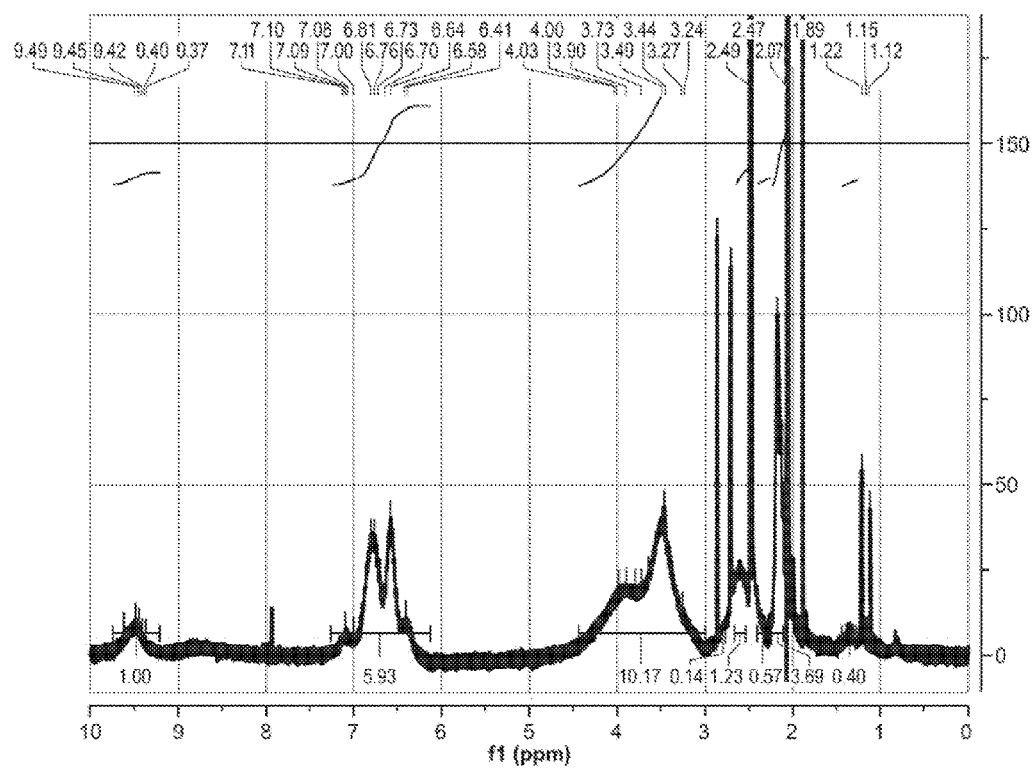

In certain embodiments, the invention relates to monomers and polymers with high-catechol content and water solubility. In certain embodiments, the invention relates to a synthetic route to preparing polymer solutions of the invention under non-corrosive conditions. In certain embodiments, the invention relates to a monomer prepared with protecting groups to prevent oxidation of a constituent catechol during the conditions of a free radical polymerization. In certain embodiments, the protecting group is acetyl. In certain embodiments, removal of the protecting group under acidic or basic conditions yields a deprotected polymer that is a charged polyanion. In certain embodiments, a polymer block comprises one acidic moiety and one catechol moiety.

In certain embodiments, the polymer is able to reversibly coordinate metal cations. In certain embodiments, the polymer may form irreversible bonds to nucleophiles, such as primary amines present on biomolecules, biopolymers, synthetic polymers, and tissue substrates. In certain embodiments, the polymer may be mixed with charged macromolecules, such as biopolymers, to from complex coacervates.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "associated with" as used herein refers to the presence of either weak or strong or both interactions between molecules. For example weak interactions may include, for example, electrostatic, van der Waals, or hydrogen-bonding interactions. Stronger interactions, also referred to as being chemically bonded, refer to, for example, covalent, ionic, or coordinative bonds between two molecules. The term "associated with" also refers to a compound that may be physically intertwined within the foldings of another molecule, even when none of the above types of bonds are present. For example, an inorganic compound may be considered as being in association with a polymer by virtue of it existing within the interstices of the polymer.

The terms "comprise" and "comprising" are used in the inclusive, open sense, meaning that additional elements may be included.

The term "including" is used to mean "including but not limited to". "Including" and "including but not limited to" are used interchangeably.

The term "polymer" is used to mean a large molecule formed by the union of repeating units (monomers). The term polymer also encompasses copolymers.

The term "co-polymer" is used to mean a polymer of at least two or more different monomers.

The term "biopolymer" is used to mean repeating units of biological or chemical moieties that is compatible with a biological system or that mimics naturally occurring polymers. Representative biopolymers include, but are not limited to oligonucleotides, polynucleotides, peptides, polypeptides, proteins, hormones, oligosaccharides, polysaccharides, lipids, glycolipids, lipopolysaccharides, phospholipids, synthetic analogues of the foregoing and combinations of the foregoing.

The term "gel" is used to mean a gelled composition, which is flexible, as opposed to a solid product, and the viscosity of which can be measured.

The term "complex coacervate" is used to mean the resulting formulation after a phase separation when two oppositely charge polyelectrolytes are mixed. The term "complex coacervate" includes an aggregate, e.g., of colloidal droplets, held together by electrostatic attractive forces.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-tirfluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

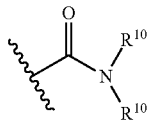

wherein each R$^{10}$ independently represent a hydrogen or hydrocarbyl group, or two R$^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

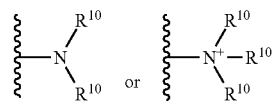

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The term "carbamate" is art-recognized and refers to a group

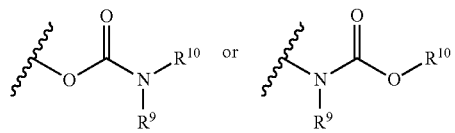

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxyl", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

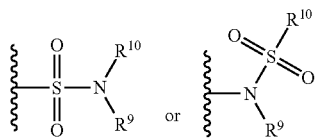

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

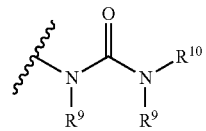

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative hydroxyl protecting groups include, but are not limited to, those where the hydroxyl group is either acylated (esterified) such as acetyl or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "ortho" is art-recognized and refers to the relationship of substituents where two substituents are bonded to two adjacent carbon atoms (i.e., vicinal).

The definition of each expression, e.g., alkyl, m, n, and the like, when it occurs more than once in any structure, is intended to be independent of its definition elsewhere in the same structure.

A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of the invention, the chemical elements are identified in accordance with the Periodic Table of the Elements, CAS version, Handbook of Chemistry and Physics, 67th Ed., 1986-87, inside cover.

Exemplary Monomers

One aspect of the invention relates to a compound represented by Formula I:

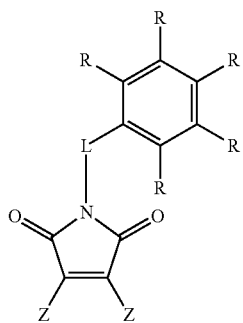

Formula I wherein, independently for each occurrence:

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl; and n is 1, 2, 3, 4, 5, or 6.

In certain embodiments, the two instances of —$OR^2$ have an ortho (i.e., vicinal) relationship. In certain embodiments, $R^1$ is hydrogen or methyl. In certain embodiments, Z is hydrogen. In certain embodiments, n is 2, 3, or 4. In certain embodiments, L is —$(C(R^1)_2)_n$—.

In certain embodiments, three instances of R represent hydrogen.

In certain embodiments, $R^2$ is acyl. In certain embodiments, $R^2$ is —$C(O)CH_3$. In certain embodiments, $R^2$ is hydrogen.

In certain embodiments, the compound is represented by:

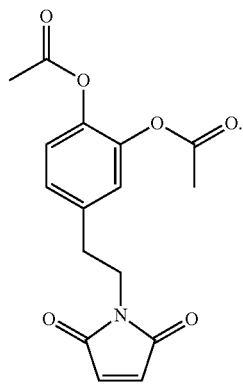 [SMILES: CC(=O)Oc1ccc(CCN2C(=O)C=CC2=O)cc1OC(C)=O]

Exemplary Methods

In certain embodiments, the invention relates to a method of preparing a polymer comprising a plurality of polymer blocks represented by Formula II:

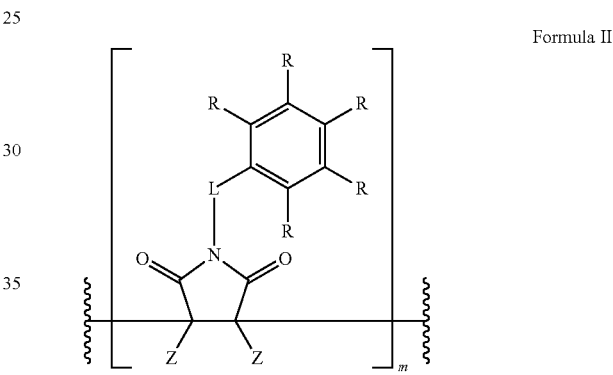

Formula II comprising the step of combining a compound of any one of claims 1-13, and a free radical initiator;

wherein, independently for each occurrence:

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl;

n is 1, 2, 3, 4, 5, or 6; and m is 1 to 500,000.

In certain embodiments, the step of combining further comprises a polymer monomer; and said polymer further comprises a plurality of polymer blocks formed from said second polymer monomer.

In certain embodiments, said free radical initiator is a peroxide or an azo compound. In certain embodiments, the free radical initiator is an azo compound selected from the group consisting of 4,4'-Azobis(4-cyanovaleric acid), 4,4'-Azobis(4-cyanovaleric acid), 1,1'-Azobis(cyclohexanecarbonitrile), 2,2'-Azobis(2-methylpropionamidine)dihydrochloride, 2,2'-Azobis(2-methylpropionitrile), and 2,2'-Azobis(2-methylpropionitrile). In certain embodiments, the free radical initiator is 2,2'-Azobis(2-methylpropionitrile). In certain embodiments, said free radical initiator is a peroxide selected from the group consisting of tert-butyl hydroperoxide, tert-butyl peracetate, cumene hydroperoxide, dicumyl peroxide, benzoyl peroxide, and tert-butyl peroxide.

Exemplary Polymers

In certain embodiments, the invention relates to a polymer, comprising a plurality of polymer blocks represented by Formula II:

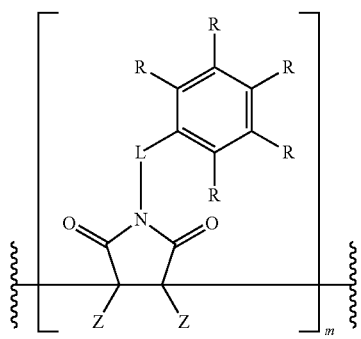

Formula II wherein, independently for each occurrence:

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl;

n is 1, 2, 3, 4, 5, or 6; and m is 1 to 500,000.

In certain embodiments, the two instances of —$OR^2$ have an ortho (i.e., vicinal) relationship. In certain embodiments, $R^1$ is hydrogen or methyl. In certain embodiments, Z is hydrogen. In certain embodiments, n is 2, 3, or 4. In certain embodiments, L is —$(C(R^1)_2)_n$—.

In certain embodiments, three instances of R represent hydrogen.

In certain embodiments, $R^2$ is acyl. In certain embodiments, $R^2$ is —$C(O)CH_3$. In certain embodiments, $R^2$ is hydrogen.

In certain embodiments, $R^1$ is hydrogen; Z is hydrogen; n is 2; L is —$(C(R^1)_2)_n$—; —$C_6(R)_5$ is 3,4-bis($R^2O$)phenyl; and $R^2$ is hydrogen or —$C(O)CH_3$.

In certain embodiments, m is 10 to 500,000; 10 to 250,000; 10 to 100,000; 10 to 50,000; 10 to 10,000; 10 to 1,000; 1,000 to 100,000; or 10,000 to 100,000.

In certain embodiments, the invention relates to a polymer, comprising a plurality of polymer blocks represented by Formula III:

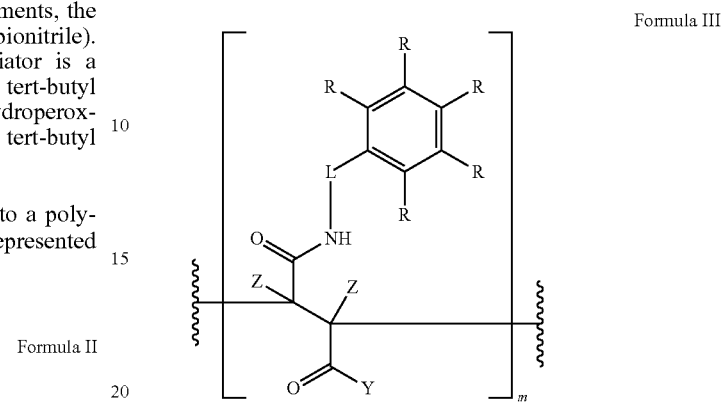

Formula III wherein, independently for each occurrence:

Y is —$OR^3$ or —$N(R^1)(R^2)$;

Z is hydrogen or optionally substituted alkyl, acyl, acyloxy, aryl, sulfonate, sulfone, sulfoxide, or sulfonamide;

L is —$(C(R^1)_2)_n$—, or —$(C(R^1)_2)_nO$—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —$OR^2$; provided that two instances of R represent —$OR^2$;

$R^1$ is hydrogen or alkyl;

$R^2$ is hydrogen or optionally substituted alkyl, acyl, or aryl;

$R^3$ is hydrogen or alkyl;

n is 1, 2, 3, 4, 5, or 6; and m is 1 to 500,000.

In certain embodiments, the two instances of —$OR^2$ have an ortho (i.e., vicinal) relationship. In certain embodiments, $R^1$ is hydrogen or methyl. In certain embodiments, Z is hydrogen. In certain embodiments, n is 2, 3, or 4. In certain embodiments, L is —$(C(R^1)_2)_n$—.

In certain embodiments, three instances of R represent hydrogen.

In certain embodiments, $R^2$ is acyl. In certain embodiments, $R^2$ is —$C(O)CH_3$. In certain embodiments, $R^2$ is hydrogen.

In certain embodiments, $R^1$ is hydrogen; Z is hydrogen; n is 2; L is —$(C(R^1)_2)_n$—; —$C_6(R)_5$ is 3,4-bis($R^2O$)phenyl; and $R^2$ is hydrogen or —$C(O)CH_3$.

In certain embodiments, m is 10 to 500,000; 10 to 250,000; 10 to 100,000; 10 to 50,000; 10 to 10,000; 10 to 1,000; 1,000 to 100,000; or 10,000 to 100,000.

In certain embodiments, Y is —$OR^3$. In certain embodiments, $R^3$ is hydrogen.

In certain embodiments, the invention relates to any one of the polymers described herein, further comprising a metal cation, wherein the metal cation is coordinated to the polymer. In certain embodiments, the metal cation is a transition metal cation. In certain embodiments, the transition metal cation is $Fe^{2+}$ or $Fe^{3+}$.

In certain embodiments, the invention relates to a polymer, comprising a first polymer block; and a second polymer block; wherein said first polymer block is a polymer of any one of the polymers comprising Formula II; and said second polymer block is a polymer of any one of the polymers comprising Formula III.

Exemplary Gels

Catechol functionalities may be utilized in the development of injectable soft-tissue fillers that can deliver slowly-crosslinking, tissue-permeable macromolecules for gradual maturation over time after implantation. Existing tissue crosslinking strategies often rely on the application of a reactive small molecule, typically offering limited flexibility in manipulating crosslinker diffusivity, reaction time, and concentration, all of which are important for controlling the stiffness and toughness of the artificial implant or tissue site over time. Single-component macromolecular crosslinkers that can bond biological molecules without the need for additional catalysts or initiators may be able to provide an improved level of control over tissue mechanics via manipulation of the polymer's molecular weight distribution, charge density, and composition of the reactive group.

In certain embodiments, the invention relates to a gel, comprising any one of the polymers described herein; and a second polymer. In certain embodiments, the invention relates to any one of the gels described herein, wherein the second polymer is a biopolymer selected from the group consisting of polypeptides, polysaccharides, and polynucleotides. In certain embodiments, the invention relates to any one of the gels described herein, wherein the second polymer is a polypeptide; and the polypeptide is an elastin-like polypeptide. In certain embodiments, the invention relates to any one of the gels described herein, wherein the second polymer is a polypeptide; and the polypeptide is a protein. In certain embodiments, the invention relates to any one of the gels described herein, wherein the second polymer is a polysaccharide; and the polysaccharide is an amino-decorated polysaccharide.

Exemplary Complex Coacervates

In certain embodiments, the invention relates to a complex coacervate, comprising a polymer of any one of the polymers comprising Formula II; and a cationic polymer. In certain embodiments, the invention relates to any one of the complex coacervates described herein, wherein the cationic polymer is a biopolymer. In certain embodiments, the invention relates to any one of the complex coacervates described herein, wherein the biopolymer is selected from the group consisting of polypeptides, polysaccharides, and polynucleotides

EXEMPLIFICATION

The invention now being generally described, it will be more readily understood by reference to the following examples, which are included merely for purposes of illustration of certain aspects and embodiments of the present invention, and are not intended to limit the invention.

Example 1

Monomer Synthesis

An exemplary monomer synthesis consists of a ring-opening reaction of maleic anhydride with dopamine, followed by ring-closing and hydroxyl-protection with acetic anhydride. See Scheme 1. A similar strategy was utilized to synthesize a maleoyl-L-histidine monomer. See Trojer, et al., Journal of Polymer Research, (2012) 19:9821-9829.

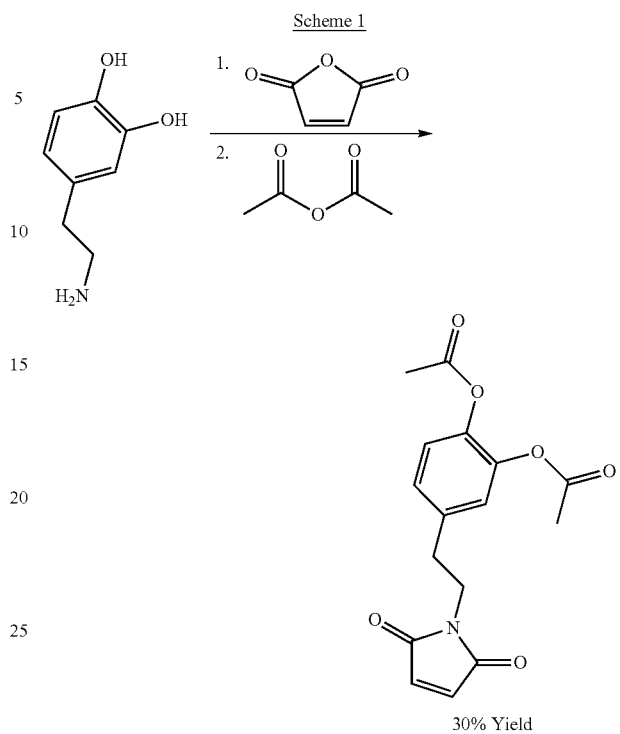

Scheme 1

30% Yield

Example 2

Polymer Synthesis and Characterization

An exemplary polymer synthesis is highlighted in Scheme 2. N-substituted maleimides polymerized under free-radical conditions form polymers with a backbone consisting of repeating succinimido groups. The polymerization of the protected N-maleimido-dopamine was demonstrated in DMF in the presence of AIBN at 80° C. The polymer was isolated by ether precipitation. The catechol sidechains are readily deprotected by TFA/HBr. Acidic conditions, in the absence of strong oxidizers, appear to be suitable for preventing catechol oxidation and crosslinking during deprotection. Additionally, ring-opening of the succinimido groups conveniently occurs under these conditions, liberating one carboxylic acid group per monomer repeat.

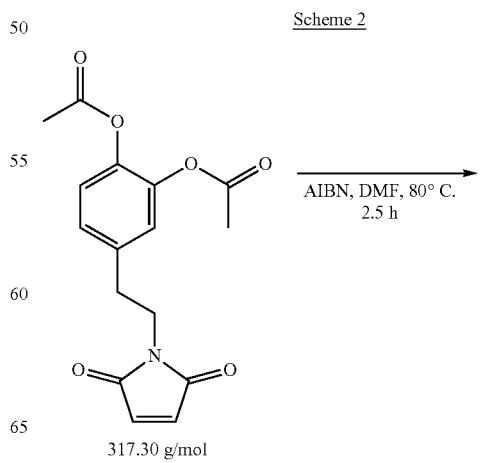

Scheme 2

AIBN, DMF, 80° C.
2.5 h 317.30 g/mol

-continued

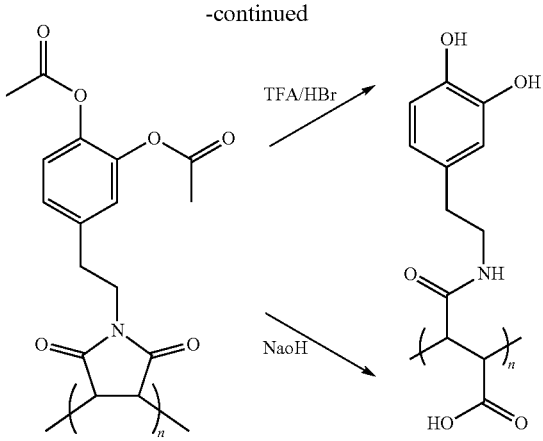

Figure 2:
FIG. 2 depicts images of: a solution of hydrolyzed poly (N-maleimido-dopamine) in dilute aqueous NaOH (panel A); and that sample after a dilute solution of $FeCl_3$ was added (panel B).
Figure 2:
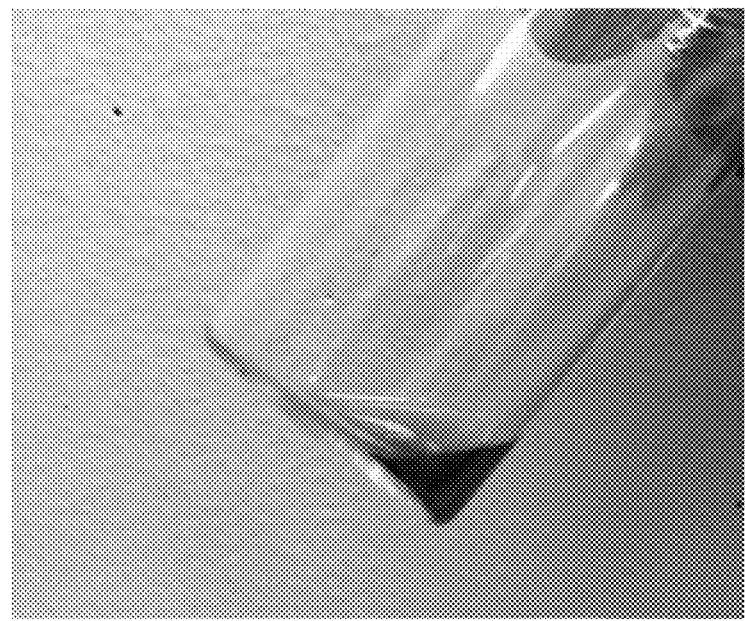

The protected polymer is insoluble in water, as expected, although it will very slowly dissolve (overnight) in the presence of NaOH, either due to slow backbone hydrolysis or slow catechol deprotection. However, the deprotected polymer rapidly dissolves under basic conditions. The polymer solution is slightly pink, and is capable of coordinating $Fe^{3+}$ ions under basic conditions, consistent with the polymer having accessible catechol moieties (FIG. 2). Precipitation or gelation was not observed under these conditions. After dissolution under basic conditions, the solution pH can be adjusted over a relatively broad range by mixing with various buffers: 250 mM bicine, pH=9; 250 mM bis-tris, pH=7; 100 mM acetate, pH=5. Cloudy solutions were observed in 250 mM formate, pH=3, which is consistent with the polymer having a $pK_a$ near that of poly(acrylic acid) ($pK_a$~4).

Example 3

Polymer Performance

Figure 3:
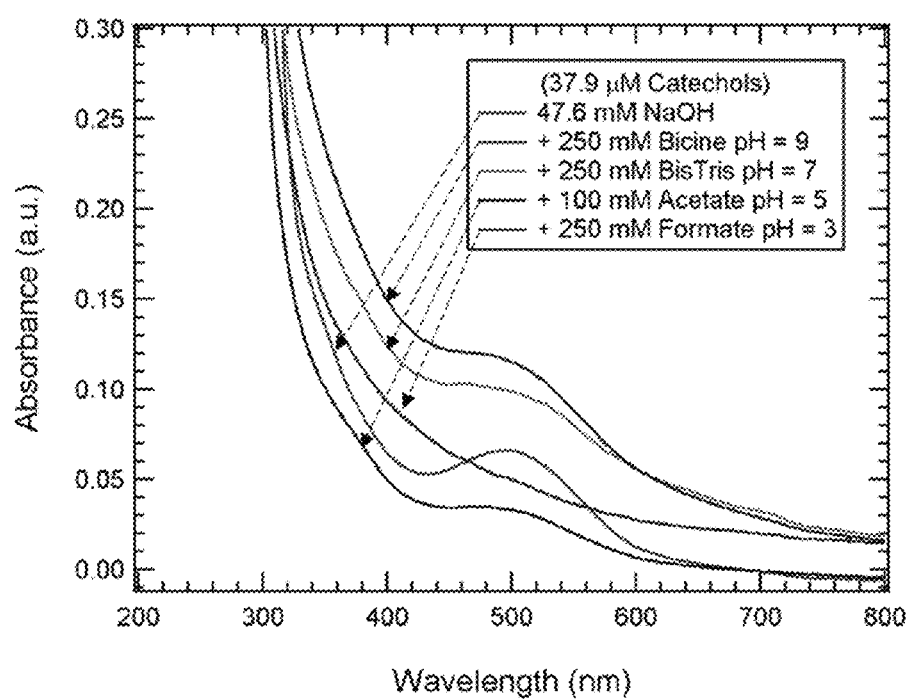
FIG. 3 depicts the pH dependence of the spectrophotometric absorbance of aqueous solutions of hydrolyzed poly (N-maleimido-dopamine).
Figure 4:
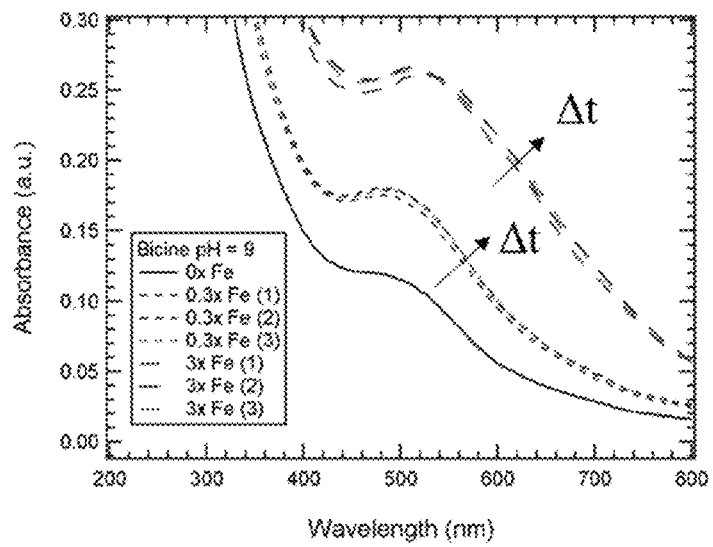
FIG. 4 depicts the pH and iron-dependent absorbance of aqueous solutions of hydrolyzed poly(N-maleimido-dopamine). The arrows indicate the trend, as a function of time (over up to 10 minutes), of changes in the absorbance spectra at the indicated conditions. The large increase in background absorbance in the 3× conditions at pH=9 (panel A), 7 (panel B), and 5 (panel C) correlate with the formation of a black precipitate. At pH=3 (panel D) all solutions were cloudy. Tris-catecholato-$Fe^{3+}$ and bis-catecholato-$Fe^{3+}$ complexes have characteristic peak absorbances at ~492 nm and ~575 nm, respectively.
Figure 4:
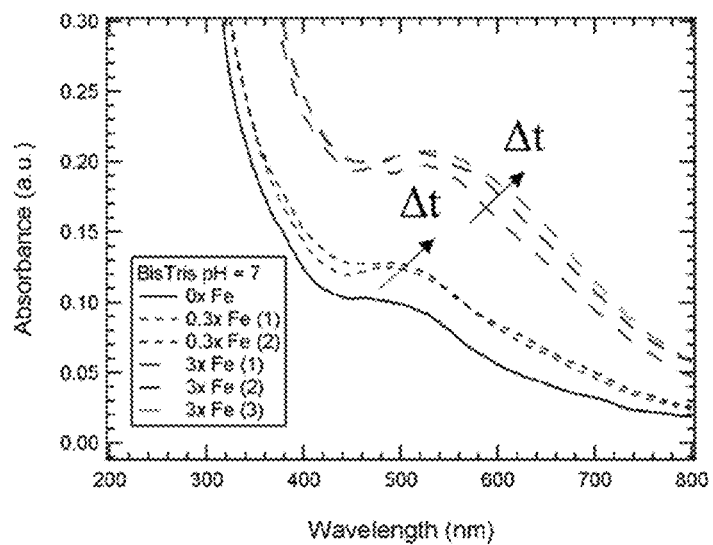
Figure 4:
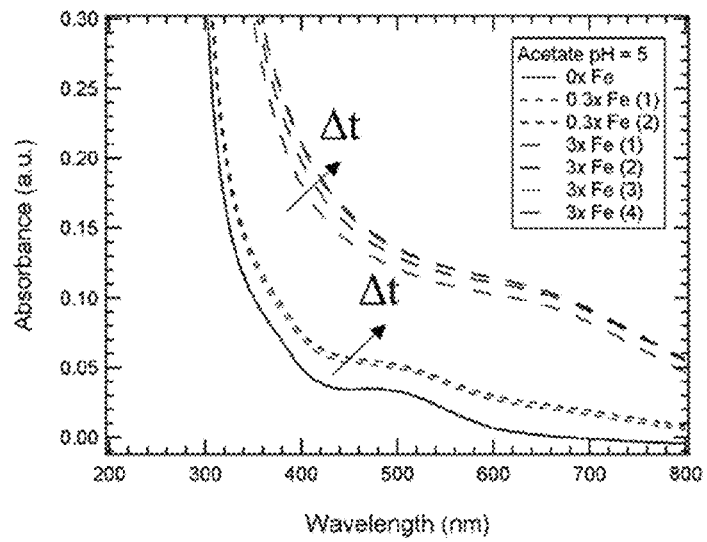
Figure 4:
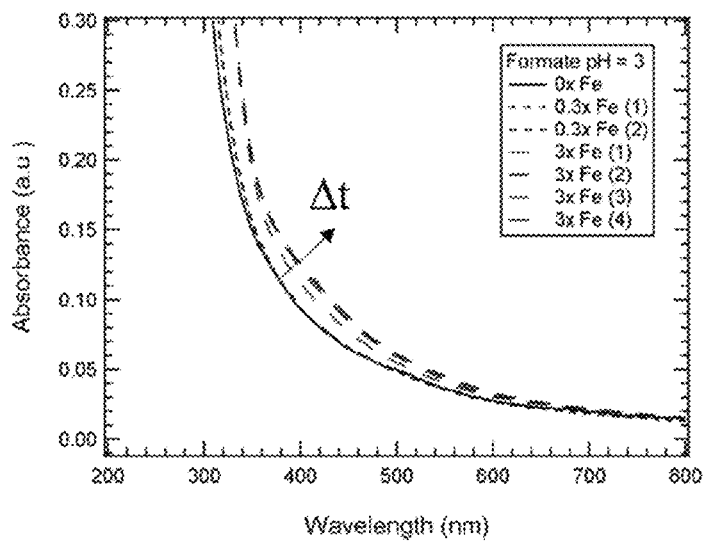

The pH and $Fe^{3+}$-dependent solution properties of the polymer of Example 2 were investigated spectrophotometrically, demonstrating the preservation of the iron-chelating capability, as well as the iron-dependent oxidation and chemical crosslinking (FIGS. 3 and 4). Solutions prepared with a roughly 3:1 catechol:$Fe^{3+}$ ratio remained clear and exhibited spectroscopic behavior typical for iron coordination; 10-times this ratio of iron led to the formation of a black precipitate, suggesting catechol oxidation and crosslinking.

Example 4

Polymer Crosslinking with Tissue-Like Macromolecules

Figure 5:
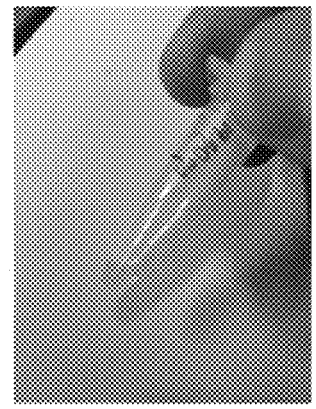
FIG. 5 depicts images of hydrated ELP powders (40% w/v): without catechol polymer (panel A), and with the catechol polymer at roughly 1:1 catechol:amine (panel B), on ice. Panel C depicts an image of the same solutions, but warmed by hand.
Figure 5:
Figure 5:
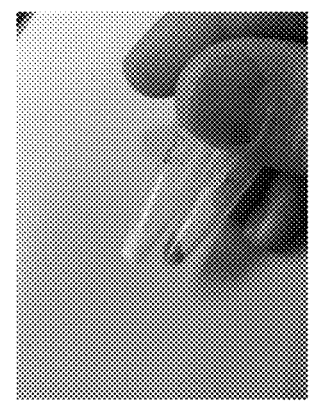

The ability to use hydrolyzed poly(N-maleimido-dopamine) to crosslink tissue-like macromolecules was investigated by preparing a dilute solution of the polymer of Example 2 and applying this to a lyophilized powder of an elastin-like polypeptide (ELP) (FIG. 5). The particular ELP had a molar mass of 30 kDa and contained two copies of the amino acid sequence KCTS at the N- and C-termini. This protein contains exactly three primary amines: two from the lysine residues at either end of the protein, and one at the N-terminus.

Figure 6:
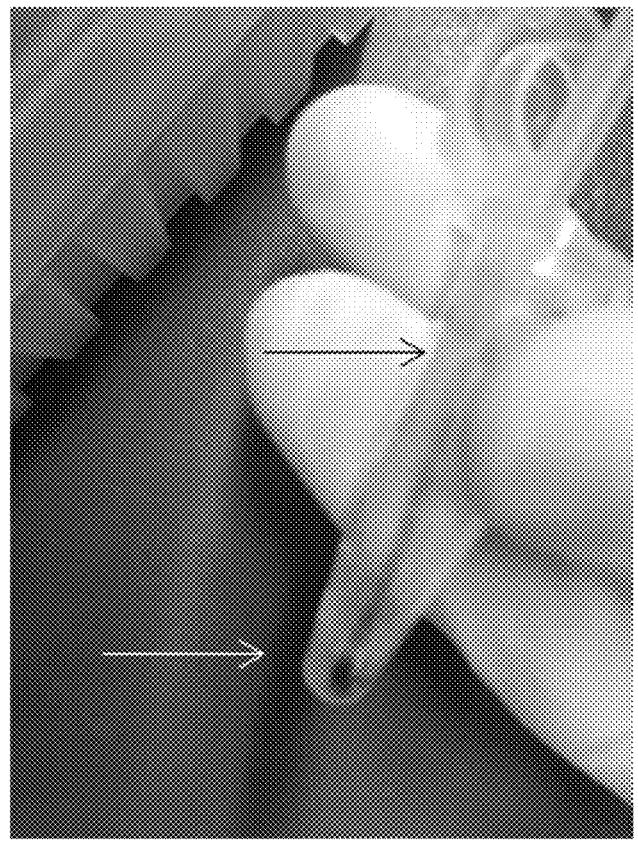
FIG. 6 depicts an image from a video recording of mechanical interrogation of the ELP solution crosslinked with a polymeric catechol. The white arrow indicates the approximate, unperturbed position of the gel surface, and the black arrow indicates the approximate position of the spatula tip.

After extended incubation on ice (3-6 hours), the solutions were probed with a plastic spatula to qualitatively examine for evidence of gelation. The solution without the catechol polymer was a viscoelastic liquid, as expected. The solution with the added catechol polymer was clearly a crosslinked, stiff gel, and even exhibited surprising adhesion to the thin plastic spatula that was used to interrogate its properties (FIG. 6). Pulling the spatula led to elongation of the gel into a fiber, and after adhesive failure, the gel retracted elastically. This gel was probed immediately after being removed from an ice bath.

After further incubation on ice (for an additional 1-3 hours), the crosslinked gels were swollen in excess water or a 30% hydrogen peroxide solution. Swelling appeared to decrease slightly in the hydrogen peroxide solution; however, under both sets of conditions the gels appeared to display decreased adherence to the plastic spatula.

Example 5

Tissue Adhesion

The deprotected polymer of Example 2 has been successfully used to adhere two pieces of hydrated porcine intenstinal tissue by direct application of lyophilized material in a reaction that proceeded overnight. Rapid crosslinking can be triggered with the addition of an oxidizing agent, such as iron (III) chloride or other agents commonly known such as periodate salts. The highly charged, anionic nature of the deprotected polymer enables it to form complex coacervates with various cationic bio- and synthetic polymers, including chitosan and polyallylamine hydrochloride, suggesting the ability to be used in layer-by-layer technologies.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A polymer, comprising a plurality of polymer blocks represented by Formula III:

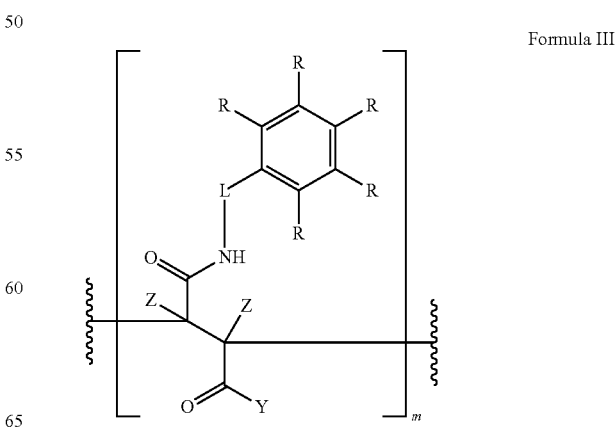

Formula III wherein, independently for each occurrence:

Y is —OR³ or —N(R¹)(R²);

Z is hydrogen or optionally substituted alkyl, acyl, acyloxy, aryl, sulfonate, sulfone, sulfoxide, or sulfonamide;

L is —(C(R¹)₂)ₙ—, or —(C(R¹)₂)ₙO—;

R is selected from the group consisting of hydrogen, hydroxyl, halogen, nitro, cyano, alkyl, alkenyl, acyl, aryl, alkylamino, acylamino, alkoxy, acyloxy, hydroxyalkyl, alkoxyalkyl, aminoalkyl, (alkylamino)alkyl, alkylthio, thioalkyl, (alkylthio)alkyl, alkynyl, carboxyl, sulfate, amino, ether, thioether, ester, amide, thioester, carbonate, carbamate, urea, sulfonate, sulfone, sulfoxide, sulfonamide, heteroaryl, carbocyclyl, heterocyclyl, aralkyl, arylalkoxy, heteroaralkyl, carbocyclylalkyl, heterocyclylalkyl, and —OR²; provided that two instances of R represent —OR²;

R¹ is hydrogen or alkyl;

R² is hydrogen or optionally substituted alkyl, acyl, or aryl;

R³ is hydrogen or alkyl;

n is 1, 2, 3, 4, 5, or 6; and m is 1 to 500,000.

2. The polymer of claim 1, wherein said two instances of —OR² have an ortho relationship.

3. The polymer of claim 1, wherein Z is hydrogen.

4. The polymer of claim 1, wherein R² is acyl.

5. The polymer of claim 1, wherein R¹ is hydrogen; Z is hydrogen; n is 2; L is —(C(R¹)₂)ₘ—; —C₆(R)₅ is 3,4-bis(R²O)phenyl; and R² is hydrogen or —C(O)CH₃.

6. The polymer of claim 1, further comprising a metal cation, wherein the metal cation is coordinated to the polymer.

7. The polymer of claim 6, wherein the metal cation is a transition metal cation.

8. The polymer of claim 7, wherein the transition metal cation is Fe²⁺ or Fe³⁺.

9. The polymer of claim 1, wherein R¹ is hydrogen or methyl.

10. The polymer of claim 1, wherein R¹ is hydrogen.

11. The polymer of claim 1, wherein n is 2, 3, or 4.

12. The polymer of claim 1, wherein n is 2.

13. The polymer of claim 1, wherein L is —(C(R¹)₂)ₙ—.

14. The polymer of claim 1, wherein three instances of R represent hydrogen.

15. The polymer of claim 4, wherein R² is —C(O)CH₃.

16. The polymer of claim 1, wherein R² is hydrogen.

17. The polymer of claim 1, wherein Y is —OR³.

18. The polymer of claim 17, wherein R³ is hydrogen.

19. The polymer of claim 1, wherein m is 10 to 100,000.

20. The polymer of claim 1, wherein m is 10,000 to 100,000.

* * * * *

UNITED STATES PATENT AND TRADEMARK OFFICE
CERTIFICATE OF CORRECTION

PATENT NO. : 9,540,462 B2  
APPLICATION NO. : 14/960799  
DATED : January 10, 2017  
INVENTOR(S) : Matthew J. Glassman et al.

Page 1 of 1

It is certified that error appears in the above-identified patent and that said Letters Patent is hereby corrected as shown below:

In the Specification

At Column 1, Line number 13, replace:
"W911NF-07-D-0004, awarded by the Army Research"

with:
--Contract Nos. W911NF-07-D-0004 and W911NF-13-D-0001, awarded by the Army Research--.

Signed and Sealed this
Twenty-eighth Day of February, 2017

Michelle K. Lee
*Director of the United States Patent and Trademark Office*